Sept. 23, 1958 F. W. ANDERSON Plant Pat. 1,755
NECTARINE TREE
Filed Feb. 3, 1958
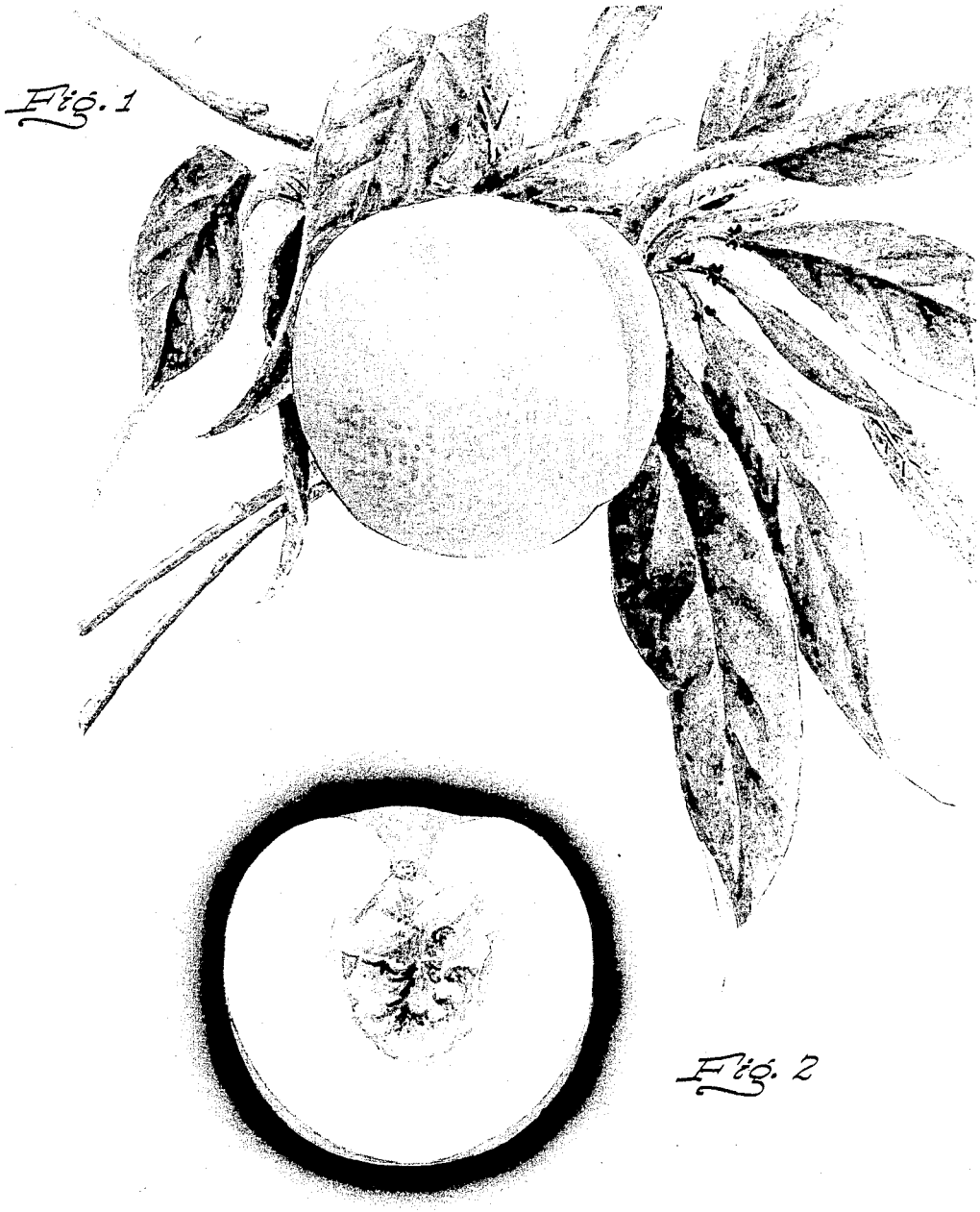
WITNESS
Addison E. Avery
INVENTOR.
Frederic W. Anderson
Webster & Webster
ATTYS.

United States Patent Office

Plant Pat. 1,755
Patented Sept. 23, 1958

1,755

NECTARINE TREE

Frederic W. Anderson, Merced, Calif., assignor to Kim Bros., a copartnership doing business under the fictitious name of Reedley Nursery, Reedley, Calif.

Application February 3, 1958, Serial No. 713,073

1 Claim. (Cl. 47—62)

This invention relates to a novel variety of nectarine tree which bears large, yellow fleshed, clingstone fruit; the variety being generally similar—in tree and fruit characteristics—to the Late Le Grand nectarine (United States Plant Patent No. 1,035), but is markedly distinctive, in comparison to the latter, by reason of a substantially later ripening period.

The fruit of the present variety ripens approximately two or three weeks later than such Late Le Grand nectarine, and thus extends the harvest season of Le Grand type nectarines well into September, after a first picking which usually begins at the end of the first week or early in the second week of such month when the variety is grown in the central valley of California.

Over a substantial number of years I have conducted an extensive plant breeding project in my experimental orchard, located near Merced, California, seeking new varieties of nectarines especially adapted to commercial growing and marketing.

The primary object of this invention—namely, the attainment of a Le Grand type nectarine having a relatively late ripening period, and which advantageously extends the harvest season of this class of fruit—was accomplished upon the origination by me, in my experimental orchard located as aforesaid, of the present variety in the following manner:

The variety is a seedling of the Late Le Grand nectarine X an unnamed and unpatented peach seedling from the Le Grand nectarine (United States Plant Patent No. 549) which I previously originated. Such unnamed seedling is known to me, and identified in my records, as the 1K45*a* peach; the latter bearing very large, late ripening fruit. Flowers of the Late Le Grand nectarine were—under conditions of control—fertilized by pollen from the above unnamed peach seedling, and the herein claimed variety of nectarine resulted from such cross. As the variety evidenced—in maturity—the desired characteristics I then selected it for further reproduction.

Subsequent to its origination and selection, as above, I have successfully asexually reproduced the variety by top-working on mature orchard trees in the above experimental orchard, and such reproductions ran true to the parent seedlings in all respects.

In the drawings:

Fig. 1 is an elevation showing one of the nectarines, together with twigs and leaves.

Fig. 2 is a sectional elevation of one of the nectarines; the view showing adherent flesh on the clingstone, which remains in place.

Referring now more specifically to the pomological details of this new and distinct variety of nectarine tree, the following is an outline description thereof; all major color plate identifications being by reference to Maerz and Paul Dictionary of Color:

Tree:
- *Size.*—Large.
- *Vigor.*—Vigorous.

- *Form.*—Spreading.
- *Production.*—Productive.

Trunk:
- *Size.*—Stocky to medium.

Branches:
- *Size.*—Stocky to medium.

Leaves:
- *Size.*—Large to medium. Average length—6⅜". Average width—1¼".
- Margin.—Crenate.
- *Petiole.*—Medium.
- *Glands.*—Average number—three to five. Alternate; reniform. Position—usually two on petiole and two or three on the blades.
- *Stipules.*—None.
- *Color.*—Top side—medium green (22–L–5). Under side—slightly lighter green (22–K–4).

Flower Buds:
- *Size.*—Medium.
- *Length.*—Medium.

Flowers:
- *Blooming period.*—Midseason. Medium compared with other varieties.
- *Size.*—Large.

Fruit:
- *Maturity when described.*—Eating ripe—September 15, 1957.
- *Date of first picking.*—September 8, 1957.
- *Date of last picking.*—September 18, 1957.
- *Size.*—Large; uniform. Average diameter axially—3". Average transversely in suture plane—3¼".
- *Form.*—Uniform; symmetrical; globose to oblong.
- *Suture.*—Distinct; extends from base over entire circumference.
- *Ventral surface.*—Rounded.
- *Cavity.*—Rounded; elongated in suture plane with suture showing on both sides. Average depth—⅝". Average breadth—¾".
- *Apex.*—Depressed.
- *Pistil point*—Lacking.

Skin:
- *Thickness.*—Medium.
- *Texture.*—Medium.
- *Tendency to crack.*—None.
- *Down.*—Wanting.
- *Color.*—Yellow (9–L–6 to 9–L–9), partially overspread with red (3–K–10 to 6–L–6, mottled and striped with red.

Flesh:
- *Texture.*—Firm; crisp; meaty.
- *Ripens.*—Even.
- *Flavor.*—Subacid.
- *Aroma.*—Distinct.
- *Eating quality.*—Good.
- *Color.*—Yellow (9–L–5).

Stone:
- *Type.*—Cling; adheres to flesh over entire surface along both dorsal and ventral edges.
- *Size.*—Medium. Average length—1 3/16". Average breadth—1⅛". Average thickness—13/16".
- *Form.*—Globose.
- *Base.*—Straight.
- *Apex.*—Rounded.
- *Sides.*—Equal.
- *Ridges.*—Rounded; interrupted.
- *Pits.*—Elongated.
- *Ventral edge.*—Thick.
- *Dorsal edge.*—Full.
- *Tendency to split.*—Slight.
- *Color.*—Mascara brown (7–L–8).

Use: Market; local; dessert; culinary; long distance shipping.
Keeping quality: Good.
Shipping quality: Good.

The tree and its fruit herein described may vary in slight detail due to climatic and soil conditions under which the variety may be grown.

The following is claimed:

A new and distinct variety of nectarine tree, as illustrated and described, bearing general resemblance in tree and fruit characteristics to the Late Le Grand nectarine, being characterized—in comparison thereto—by ripening two to three weeks later, the first picking normally beginning at the end of the first week or early in the second week of the month of September when grown in the central valley of California.

No references cited.